US009655566B2

United States Patent
Auchi et al.

(10) Patent No.: US 9,655,566 B2
(45) Date of Patent: May 23, 2017

(54) BIOLOGICAL INFORMATION MEASUREMENT AND DISPLAY APPARATUS

(71) Applicant: NIHON KOHDEN CORPORATION, Tokyo (JP)

(72) Inventors: Ryota Auchi, Tokyo (JP); Kazuya Nagase, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 168 days.

(21) Appl. No.: 14/642,978

(22) Filed: Mar. 10, 2015

(65) Prior Publication Data

US 2015/0257714 A1    Sep. 17, 2015

(30) Foreign Application Priority Data

Mar. 13, 2014    (JP) ................................ 2014-050714

(51) Int. Cl.
*A61B 5/00* (2006.01)
*G06F 19/00* (2011.01)

(52) U.S. Cl.
CPC ................ *A61B 5/743* (2013.01); *A61B 5/72* (2013.01); *A61B 5/7425* (2013.01); *A61B 5/7445* (2013.01); *G06F 19/3406* (2013.01); *G06F 19/3487* (2013.01); *A61B 2560/0475* (2013.01)

(58) Field of Classification Search
CPC . A61B 2560/0475; A61B 5/72; A61B 5/7425; A61B 5/743; A61B 5/7445; G06F 19/3406; G06F 19/3487

See application file for complete search history.

(56) References Cited

U.S. PATENT DOCUMENTS

| 7,285,090 | B2 * | 10/2007 | Stivoric | .................. A61B 5/01 128/905 |
| 2011/0080293 | A1 | 4/2011 | Tanishima et al. | |
| 2014/0031639 | A1 | 1/2014 | Toyomura et al. | |

FOREIGN PATENT DOCUMENTS

JP    2011-98189 A    5/2011

* cited by examiner

*Primary Examiner* — George Manuel
(74) *Attorney, Agent, or Firm* — Pearne & Gordon LLP

(57) ABSTRACT

A biological information measurement and display apparatus includes: a measuring unit measuring biological information; a first processor operating on a first operating system, and arithmetically processing the biological information measured by the measuring unit, to produce a calculation process signal; a second processor operating on a second operating system, being communicable with the first processor, and editing and processing the calculation process signal transmitted from the first processor, to produce an edition process signal; and an output controller receiving the calculation process signal produced by the first processor, and the edition process signal produced by the second processor, and outputting the received calculation process signal and the received edition process signal, the calculation process signal and the edition process signal output from the output controller being displayed in real time on a displaying unit.

8 Claims, 2 Drawing Sheets

BIOLOGICAL INFORMATION MEASUREMENT AND DISPLAY APPARATUS

CROSS-REFERENCE TO RELATED APPLICATION(S)

This application is based upon and claims the benefit of priority from prior Japanese patent application No. 2014-050714, filed on Mar. 13, 2014, the entire contents of which are incorporated herein by reference.

BACKGROUND

The presently disclosed subject matter relates to a biological information measurement and display apparatus for measuring biological information of a subject, and displaying the measured biological information on a displaying unit.

There is a bedside monitor which measures biological information of a subject, and which displays the measured biological information as waveform information or numerical information. For example, JP-A-2011-098189 discloses a bedside monitor which can display not only biological information detected from the patient on a displaying unit, but also a vital alarm that is output in abnormality of the biological information, a technical alarm that is output in abnormality of the monitor, a sensor, the measurement environment, or the like, and responding information that corresponds to the vital alarm or the technical alarm, on the displaying unit.

In bedside monitors such as the bedside monitor disclosed in JP-A-2011-098189, a built-in OS (Operating System) which is built-in in order to realize a specific function for measuring waveform information and numerical information related to predetermined biological information is often employed as basic software for managing a system. Therefore, such a bedside monitor is excellent in performance of stably measuring and displaying on predetermined biological information without causing freeze, but lacks in flexibility of expansion of functions such as that an analysis application is later added, or that composite information which requires complex processing is additionally displayed. Consequently, it is difficult to apply desired information other than the predetermined biological information to clinical practice.

SUMMARY

The presently disclosed subject matter may provide a biological information measurement and display apparatus in which the measurement function can be flexibly expanded while ensuring the reliability of the measurement operation.

The biological information measurement and display apparatus may comprise: a displaying unit; a measuring unit which is configured to measure biological information; a first operating system; a second operating system; a first processor which is configured to operate on the first operating system, and which is configured to arithmetically process the biological information measured by the measuring unit, to produce a calculation process signal; a second processor which is configured to operate on the second operating system, which is communicable with the first processor, and which is configured to edit and process the calculation process signal transmitted from the first processor, to produce an edition process signal; and an output controller which is configured to receive the calculation process signal produced by the first processor, and the edition process signal produced by the second processor, and which is configured to output the received calculation process signal and the received edition process signal, the calculation process signal and the edition process signal output from the output controller being displayed in real time on the displaying unit.

The biological information measurement and display apparatus may further comprise: a library which is communicable with the first processor and the second processor, and which is configured to store custom application software, and the second processor may receive the calculation process signal through the library, and produce the edition process signal by using the custom application software.

The edition process signal may be a signal which is produced by editing and processing a plurality of kinds of calculation process signals measured by a plurality of the measuring units.

Display contents of the edition process signal may be displayed in a manner visually distinguishable from the display contents of the calculation process signal.

Display contents of the edition process signal may be displayed in a circumferential region of the displaying unit.

DETAILED DESCRIPTION OF EXEMPLARY EMBODIMENTS

Hereinafter, an embodiment of the biological information measurement and display apparatus of the presently disclosed subject matter will be described in detail with reference to the drawings.

Figure 1:
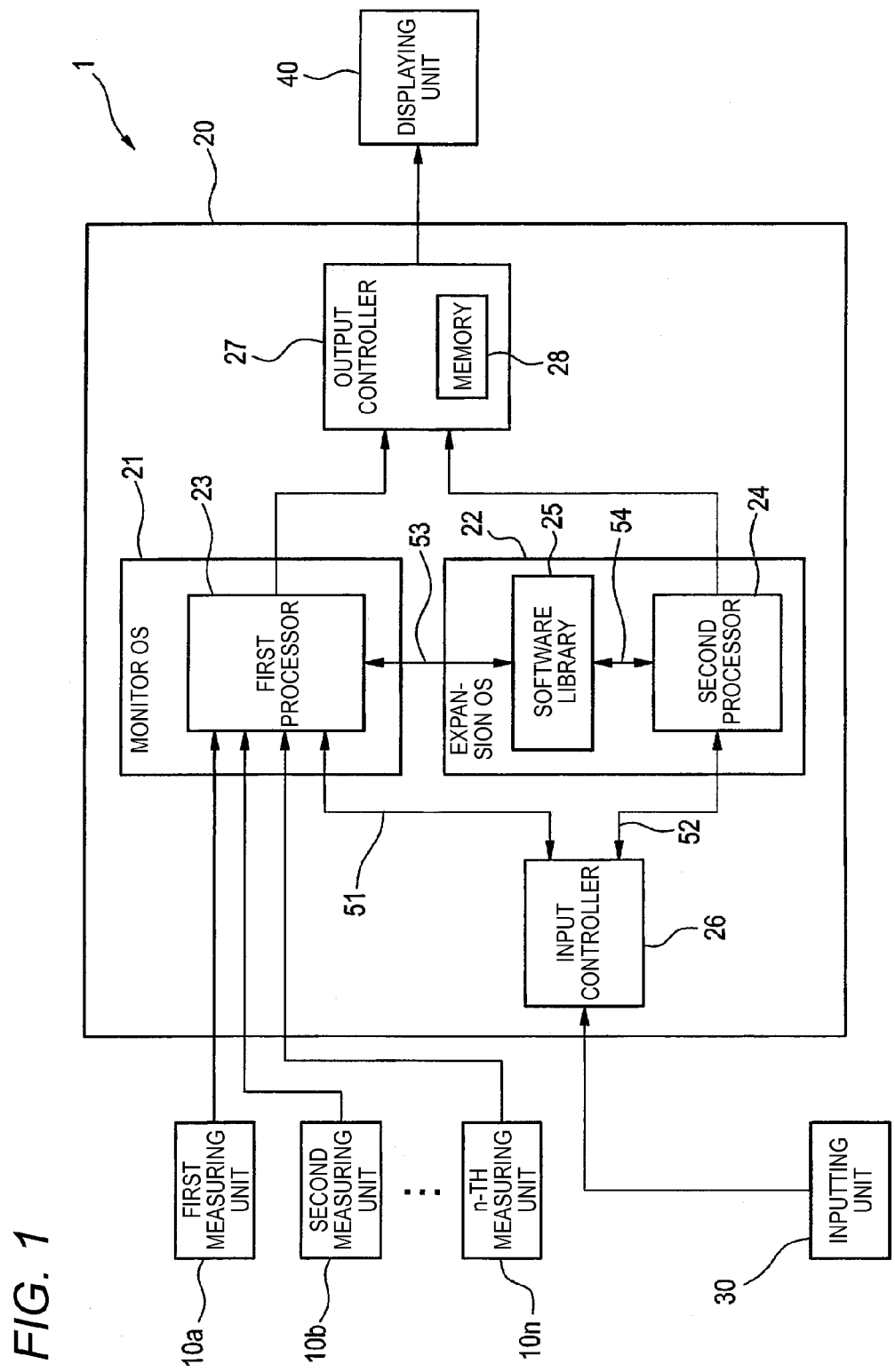
FIG. 1 is a functional block diagram showing the configuration of a biological information measurement and display apparatus of an embodiment of the presently disclosed subject matter.

FIG. 1 is a functional block diagram showing the configuration of a biological information measurement and display apparatus 1 of an embodiment of the presently disclosed subject matter. The biological information measurement and display apparatus 1 is an apparatus which is to be disposed for each of subjects, and means a so-called bedside monitor which performs a measurement, calculation process, displaying, and the like on biological information.

As shown in FIG. 1, the biological information measurement and display apparatus 1 is configured by measuring units 10a, 10b, ..., 10n, an apparatus body unit 20, an inputting unit 30, and a displaying unit 40. The apparatus body unit 20 includes a monitor OS (an example of the first operating system) 21, an expansion OS (an example of the second operating system) 22, a first processor 23, a second processor 24, a software library (an example of the library) 25, an input controller 26, an output controller 27, and a memory 28.

The measuring units 10a, 10b, ..., 10n are components for measuring biological information of the subject, and connected to the first processor 23. The measuring unit 10a, 10b, ..., 10n include various sensors including electrodes, a cuff, and the like which are to be attached to or inserted into the subject, and acquire signals related to biological information through the sensors. The measuring units 10a, 10b, ..., 10n convert the acquired biological information into electrical signals, and output the converted electrical signals to the first processor 23.

Although the measuring units 10a, 10b, . . . , 10n are disposed in the embodiment shown in FIG. 1, the number of the measuring units may be determined in accordance with that of sets of biological information to be measured. Examples of the biological information to be measured are the heart rate, the blood pressure, the oxygen saturation, the respiratory rate, the body temperature, the electrocardiogram, and the central venous pressure.

The monitor OS 21 is basic software for providing functions of controlling programs, displaying a screen, operating files, and the like. As the monitor OS 21, employed is a built-in OS which can execute specific functions of measuring waveform data, numerical data, and the like related to biological information of the subject. A built-in OS executes a predetermined specific function. In a built-in OS, hence, there is a less possibility that the process operation stops (freezes) as compared with a general-purpose OS (such as Windows, Mac OS, or Linux (these are registered trademarks), and it is possible to realize a stable and highly reliable process operation.

Similarly with the monitor OS 21, the expansion OS 22 is basic software for providing functions of controlling programs, displaying a screen, operating files, and the like. As the expansion OS 22, employed is a general-purpose OS (such as Windows, Mac OS, or Linux (these are registered trademarks) which is used in a personal computer (PC). A general-purpose OS has high expandability such as compliance with new application software, that with new peripheral device management, and that with multi-language operation.

The first processor 23 operates on the monitor OS 21, and performs a calculation process on the biological information. The first processor 23 is communicably connected to the input controller 26 via a bus line 51, and performs the process based on a control signal transmitted from the input controller 26. The control signal is a signal which is input from the inputting unit 30, or specifically an instruction signal which is produced in response to an operation by the medical person. Based on the instruction signal input by the medical person, the first processor 23 arithmetically processes the biological information measured by the measuring units 10a, 10b, . . . , 10n, to produce calculation process signals.

For example, the first processor 23 measures waveform and numerical data (for example, the blood pressure, the body temperature, the oxygen concentration, the carbon dioxide concentration, the cardiac output, and the like) which are measured by the measuring units 10a, 10b, . . . , 10n, and which are related to various sets of biological information. Moreover, the first processor 23 produces lists and graphs of the measurement values based on the measured numerical data. The first processor 23 determines whether the measurement values indicate respective abnormal values (for example, values which exceed preset thresholds) or not, and, if it is determined that either one of the measurement values indicates the corresponding abnormal value, produces an alarm display. The first processor 23 outputs signals of the various numerical data, the lists and graphs of the measurement data, the abnormality alarm display, and the like, as the calculation process signals to the output controller 27. The first processor 23 stores data such as those of the calculation process signals, and those received from the measuring units 10a, 10b, . . . , 10n, the input controller 26, and the second processor 24, in a storage unit (a memory) which is not shown.

In many cases, the biological information signals which are supplied from the measuring units 10a, 10b, . . . , 10n to the first processor 23 contain signals of the kinds which are always and continuously measured from the subject. Therefore, the first processor 23 which processes the signals is caused to operate on the monitor OS 21 having high reliability of process operation, whereby the outputs of biological information can be obtained continuously and stably.

The second processor 24 operates on the expansion OS 22, and performs an edition process on the biological information. The second processor 24 is communicably connected to the input controller 26 via a bus line 52, and performs the process based on a control signal transmitted from the input controller 26. The control signal is a signal which is supplied from the inputting unit 30, or specifically an instruction signal which is produced in response to an operation by the medical person. Based on the instruction signal input by the medical person, the second processor 24 performs an editing process such as processing, analysis, or the like on the calculation process signals transmitted from the first processor 23, to produce edition process signals.

For example, the second processor 24 edits one of the calculation process signals produced from biological information, or a combination of a plurality of calculation process signals, to produce edition process signals in which a sophisticated graphics process such as biological analysis graphs, a statistical process of data, and display decoration are performed. The edition process signals are produced by using custom application software which is previously and uniquely produced for treatment or research by the medical person. The second processor 24 outputs signals of the biological analysis graphs, the statistical process of data, and the image color decoration, as the edition process signals to the output controller 27. The second processor 24 stores data such as those of the edition process signals, and those received from the input controller 26 and the first processor 23 in a storage unit (a memory, an HDD, or the like) which is not shown.

The second processor 24 is communicably connected further to the first processor 23 through the software library 25 which will be described later. The second processor 24 and the first processor 23 transmit to and receive from each other through the software library 25, signals such as the edition process signals which are produced by the second processor 24, the control signal which is transmitted from the input controller 26 to the second processor 24, the calculation process signals which are produced by the first processor 23, and the control signal which is transmitted from the input controller 26 to the first processor 23.

A biological analysis graph, a result of a statistical process of data, display color decoration, and the like require a sophisticated graphics process, usually need a large information capacity, and hence take a long process time. Therefore, the second processor 24 which processes the signals is caused to operate on the expansion OS 22 having high expandability and versatility, whereby an output of the graphical display can be obtained in real time.

In the communication between the first processor 23 and the second processor 24 through the software library 25, in the case where the occurrence of the operation stop state (abnormal state such as freeze) on the side of the expansion OS 22 is detected, the first processor 23 may perform a process of reducing the number of communications with the second processor 24 through the software library 25 (or interrupting at least a part of the communications), in order to prevent the unit from being affected by the state.

The software library 25 operates on the expansion OS 22, and is communicably connected respectively to the second processor 24 via a bus line 54, and to the first processor 23 via a bus line 53. The software library 25 collectively stores a plurality of kinds of application software. The application software includes custom application software which is uniquely developed by the medical person in order to diagnose or treat the symptom of the subject, or make medical research. An example of such custom application software is software for editing one or a combination of plural of the various kinds of biological information measured by the measuring units 10a, 10b, . . . , 10n to produce edition data in which new desired edition biological information is used as an index. The edition data include modes such as biological analysis graphs, a statistical process of data, and display color decoration. The software library 25 is configured so that newly produced custom application software can be additionally stored.

The output controller 27 is configured by a graphics chip (for example, a video chip) which is an integrated circuit for processing an image. The output controller 27 can simultaneously receive a plurality of signals, and, in the embodiment, receives the calculation process signals produced by the first processor 23, and the edition process signals produced by the second processor 24. The output controller 27 performs a process of outputting the received calculation and edition process signals to the displaying unit 40. The output controller 27 can output both of the received calculation and edition process signals, or a selected one of the signals. In the case where the output controller 27 receives only one of the calculation process signals and the edition process signals, the unit may output only the received signals.

Furthermore, the output controller 27 prepares data for rewriting the image displayed on the displaying unit 40, and performs a process of placing a window screen which is to be displayed on the displaying unit 40. In the case where the output controller 27 receives both of the calculation and edition process signals, the unit determines display positions on the displaying unit 40 where images related to the signals are to be displayed. These images may be displayed so as to be placed in the same window screen, or displayed in two different window screens in a pop-up manner. The image display mode is determined in accordance with an instruction signal which is input by the medical person through the inputting unit 30. At this time, preferably, the display contents of the edition process signals may be displayed in a manner in which the contents are visually clearly distinguishable from those of the calculation process signals. Similarly with the calculation process signals, the edition process signals are displayed in real time on the displaying unit 40.

In order to display the measured biological information as images on the displaying unit 40, the output controller 27 stores data of the calculation and edition process signals, as the data for rewriting the image in the storage unit (memory, HDD, or the like) 28 disposed in the output controller 27.

The input controller 26 is connected to the inputting unit 30, and performs a process of converting the instruction signal which is input from the inputting unit 30, to the control signal for controlling the first processor 23 and the second processor 24. The input controller 26 is communicably connected to the first processor 23 via the bus line 51, and further to the second processor 24 via the bus line 52. The input controller transmits the control signal to the first processor 23 and the second processor 24, and receives a replay signal and instruction signal which are transmitted from the first processor 23 and the second processor 24.

The signals which are to be transmitted from the input controller 26 to the first processor 23 include, for example, a control signal instructing which one of the sets of biological information measured by the measuring units is output as the calculation process signal, that instructing that the communication with the second processor 24 is to be interrupted or restarted, and the like.

The control signals which are to be transmitted from the input controller 26 to the second processor 24 include, for example, a control signal instructing that the calculation process signal received from the first processor 23 is subjected to analysis, edition, and the like to produce the edition process signal. Furthermore, the control signals include, for example, a control signal for controlling the operation of the first processor 23 through the software library 25, that instructing that the communication with the first processor 23 is to be interrupted or restarted, and the like. The control signal for controlling the operation of the first processor 23 through the software library 25 has similar contents as those of the control signal which is transmitted from the input controller 26 to the first processor 23.

Signals which are received by the input controller 26 from the first processor 23 include, for example, a signal notifying of the operation stop state of the expansion OS 22, and that indicating through which one of the bus lines 51, 52 the control signal of the input controller 26 is to be transmitted. Signals which are received by the input controller 26 from the second processor 24 include, for example, a signal notifying that the second processor 24 receives the calculation process signal from the first processor 23 through the software library 25.

In the case where the expansion OS 22 normally operates (does not freeze), the input controller 26 transmits the instruction signal sent from the inputting unit 30, to the second processor 24 through the bus line 52. The instruction signal which is transmitted to the second processor 24 is further transmitted to the first processor 23 through the software library 25.

By contrast, in the case where the expansion OS 22 or the second processor 24 stops the operation (freezes), the input controller 26 transmits the instruction signal sent from the inputting unit 30, to the first processor 23 through the bus line 51. In this case, the input controller 26 detects that freeze occurs in the expansion OS 22 or the second processor 24, based on an abnormality detection signal which is transmitted from the first processor 23. The first processor 23 detects the abnormal state of the second processor 24, i.e., the freeze state of the expansion OS 22 or the second processor 24, based on the contents of the communication with the second processor 24 through the software library 25, and transmits the abnormality detection signal indicating that an abnormality is detected, to the input controller 26 through the bus line 51.

The input controller 26 which receives the abnormality detection signal performs a switching process in which the transmission of the control signal from the input controller 26 to the second processor 24 through the bus line 52 is stopped, and the control signal is transmitted to the first processor 23 through the bus line 51. In order to prevent the first processor 23 from being affected by the freeze state of the expansion OS 22 or the second processor 24, the first processor performs a process of reducing the number of communications with the second processor 24 through the software library 25 (or interrupting the communications).

The inputting unit 30 is used for operating the operation setting of the apparatus body unit 20, and receives an operation input by the medical person. The inputting unit 30 may be configured by a keyboard, a mouse, a touch panel, or the like. Examples of specific operation contents are selection and setting of information (for example, waveform data, numerical data, a biological analysis graph, a result of a statistical process of data, and display color decoration) which is to be displayed on the displaying unit 40, and those of a signal which is to be output from the output controller 27.

According to the control by the output controller 27, the displaying unit 40 can display biological information related to both or either of the calculation process signal output from the first processor 23, and the edition process signal output from the second processor 24.

Next, the biological information which is displayed on the displaying unit 40 will be described in association with FIG. 1.

Figure 2:
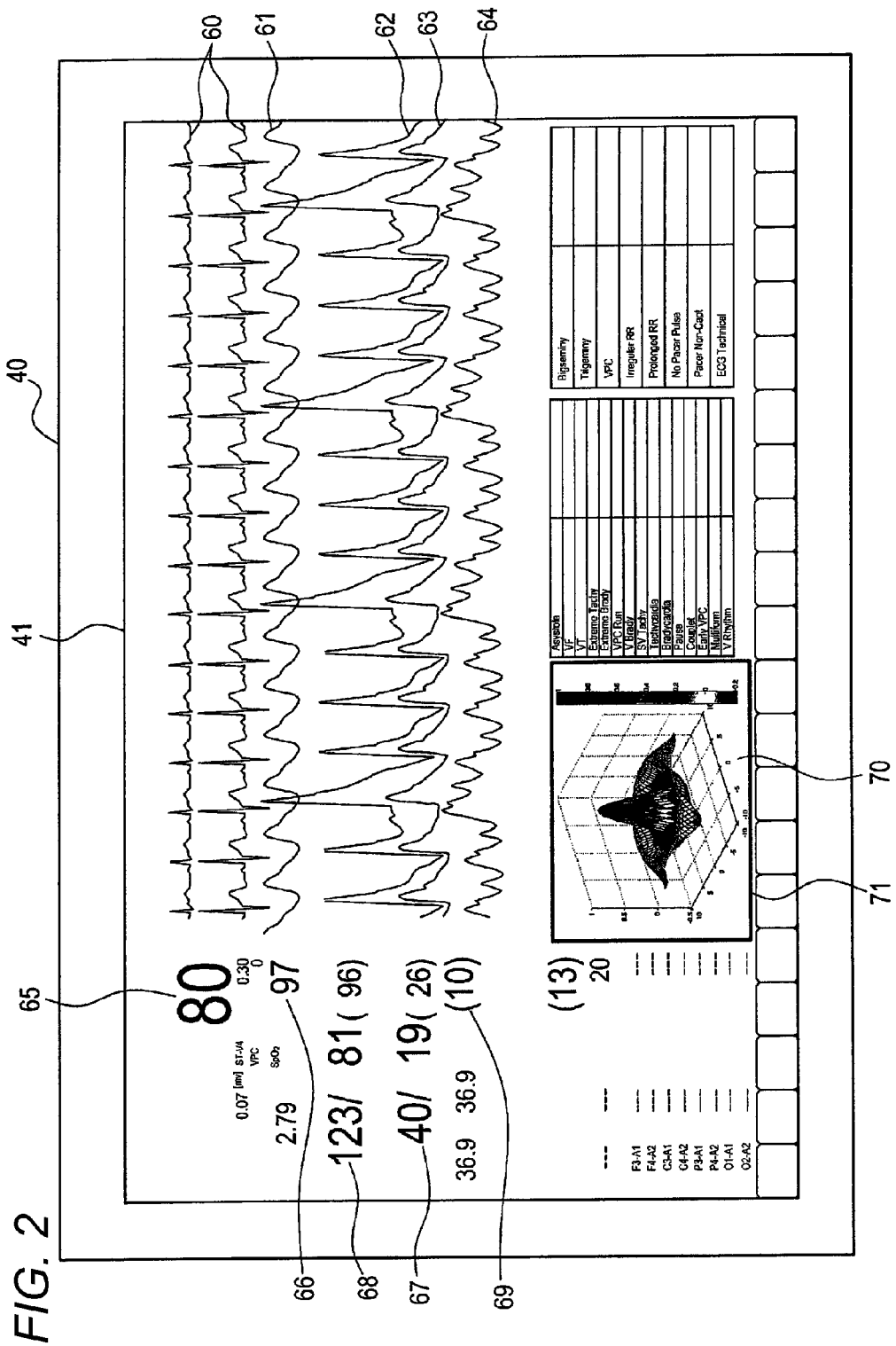
FIG. 2 is a view showing a mode of calculation and edition process signals which are displayed on a displaying unit.

FIG. 2 shows a mode of waveform and numerical data based on the calculation process signal, and a biological analysis graph based on the edition process signal.

As shown in FIG. 2, waveform data 60 to 64 of biological information, numerical data 65 to 69 related to the waveform data, a biological analysis graph 70, and the like are displayed in a window screen 41 on the displaying unit 40. For example, the reference numerals 60 and 65 represent the heart rate, 61 and 66 represent the oxygen saturation, 62 and 67 represent the pulmonary arterial pressure, 63 and 68 represent the aortal pressure, and 64 and 69 represent the central venous pressure.

The biological information measured by the measuring units 10a, 10b, . . . , 10n is input to the first processor 23. The first processor 23 arithmetically processes the sets of biological information to produce the calculation process signals, and transmits the produced calculation process signals to the output controller 27. The calculation process signals which are produced by the first processor 23 are signals for the waveform data 60 to 64 and the numerical data 65 to 69.

BY using the application software stored in the software library 25, the second processor 24 receives the calculation process signals which are produced by the first processor 23, edits and processes the signals, and produces the edition process signals. The produced edition process signals are transmitted to the output controller 27. The edition process signals which are produced by the second processor 24 are signals for the biological analysis graph 70.

The output controller 27 causes the received signals for the waveform data 60 to 64, the numerical data 65 to 69, and the biological analysis graph 70 to be displayed in the same window screen 41 of the displaying unit 40. The output controller 27 further causes the biological analysis graph 70 to be displayed in the circumferential region of the window screen 41 so as not to overlap with the display contents of the waveform data 60 to 64 and the numerical data 65 to 69. Moreover, the output controller 27 causes the circumference of the biological analysis graph 70 to be surrounded by a thick frame 71 so that the biological analysis graph 70 can be easily recognized as an index for edition biological information which is produced by a specific medical person. The output controller 27 causes the biological analysis graph 70 to be displayed in real time similarly with the waveform data 60 to 64 and numerical data 65 to 69 which are currently under measurement. Alternatively, the biological analysis graph 70 may be displayed in a pop-up manner in a window screen different from that in which the waveform data 60 to 64 and the numerical data 65 to 69 are displayed. The display of the biological analysis graph 70 on the displaying unit 40 may be turned ON or OFF in accordance with the instruction signal which is sent from the inputting unit 30.

In the case where the medical person makes diagnosis or treatment on the symptom of the subject by using a measurement apparatus such as a bedside monitor, it is usual to employ the method in which the diagnosis or the treatment is performed while checking biological information measured from the subject, on a monitor. However, the kinds of biological information which can be measured are previously determined depending on the used measurement apparatus, and it is difficult to check measurement data in which other biological information, for example, new biological information different from the existing biological information is used as an index. When such data are to be measured, therefore, data of biological information measured by the measurement apparatus must be once extracted as serial data into, for example, an external PC, and desired data must be produced by processing or analyzing the extracted data. Also in the case where data of biological information measured from the subject are to be processed or analyzed to be used in medical research, the data must be similarly extracted to the outside, and then processed or analyzed. Therefore, a certain amount of time must elapse before desired data are acquired, and it is impossible to perform diagnose while comparing the current condition of the subject with the desired data. The kinds of data which are to be extracted to the outside to be subjected to a process or the like are specified to those which are selected by each medical person. Therefore, it is difficult to perform a comprehensive comparison with the whole measurement data.

According to the biological information measurement and display apparatus 1 of the embodiment, by contrast, the waveform data 60 to 64 and numerical data 65 to 69 of the biological information which are measured by the measuring units 10a, 10b, . . . , 10n, and the biological analysis graph 70 which is desirably edited and processed based on the biological information can be displayed in real time on the same displaying unit 40. Therefore, the medical person can check the biological analysis graph 70 while observing the current condition of the subject. Moreover, the medical person can perform a comparison while time-series correlating the waveform data 60 to 64 and numerical data 65 to 69 of other currently measured biological information with the biological analysis graph 70, and check also their relationships. Therefore, a comprehensive comparative evaluation is enabled, and a diagnosis can be performed more rapidly and correctly. When the data of the biological analysis graph 70 which are edited and processed in accordance with the condition of the subject are compared with other data, it is possible to correctly know in real time how the condition transitions. Therefore, the data can be used as research data for a medical person.

The biological analysis graph 70 which is configured by the edition process signals can be produced by using the custom application software which is previously stored in the software library 25. The custom application software is an application which is uniquely developed and produced by each medical person in accordance with the condition of the subject or the research problem of the medical person. Therefore, the medical person can acquire promptly and surely data based on the biological analysis graph 70 which is a new desired index. Consequently, the acquired data can be used as research data for the medical person.

In addition to the waveform data 60 to 64 and numerical data 65 to 69 related to existing biological information, also the biological analysis graph 70 which is a customize parameter that is obtained by editing and processing one or a plurality of the waveform data 60 to 64 and the numerical data 65 to 69 can be displayed on the displaying unit 40. Therefore, each medical person can structure a new guideline which further clarifies the contents of the treatment to be performed on the subject, by using the new customize parameter which is based on the unique thinking of the person, and perform correct treatment.

The biological analysis graph 70 which is uniquely produced for the purpose of research or treatment by the medical person is displayed in a manner visually distinguishable from the display contents of the waveform data 60 to 64 and the numerical data 65 to 69. Therefore, the kind of the displayed information can be easily recognized, and the security of the procedure on the subject can be ensured.

Since the biological analysis graph 70 which is uniquely produced by the medical person is displayed in the circumferential region of the displaying unit 40, the waveform data 60 to 64 and numerical data 65 to 69 of the biological information which is continuously measured can be displayed in a region of the displaying unit 40 which can be easily recognized. According to the configuration, the display contents of the waveform data 60 to 64 and the numerical data 65 to 69 can be recognized easily and correctly, and the security of the procedure on the subject can be ensured.

The process related to the waveform data 60 to 64 and numerical data 65 to 69 of the biological information which is continuously measured is performed on the monitor OS 21, the biological analysis graph 70 which has a large amount of data requiring complex analysis and processing is processed on the expansion OS 22 that is different from the monitor OS 21. Irrespective of the operation state (stop due to freeze) of the expansion OS 22, therefore, the waveform data 60 to 64 and numerical data 65 to 69 related to the biological information can be surely measured and displayed. Consequently, the security of the treatment can be ensured.

The invention is not limited to the above-described embodiment, and may be adequately subjected to modifications, improvements, and the like. In addition, the materials, shapes, dimensions, values, forms, numbers, places, and the like of the components of the above-described embodiment are arbitrary and not limited insofar as the invention is achieved.

For example, a configuration may be employed where, in clinical practice in which the waveform data 60 to 64 and numerical data 65 to 69 related to biological information of the subject are measured, the editing process of performing processing, analysis, and like on the calculation process signals is conducted through the inputting unit 30, whereby the edition process signal can be produced.

According to the presently disclosed subject matter, there is provided a biological information measurement and display apparatus comprising: a displaying unit; a measuring unit which is configured to measure biological information; a first operating system; a second operating system; a first processor which is configured to operate on the first operating system, and which is configured to arithmetically process the biological information measured by the measuring unit, to produce a calculation process signal; a second processor which is configured to operate on the second operating system, which is communicable with the first processor, and which is configured to edit and process the calculation process signal transmitted from the first processor, to produce an edition process signal; and an output controller which is configured to receive the calculation process signal produced by the first processor, and the edition process signal produced by the second processor, and which is configured to output the received calculation process signal and the received edition process signal, the calculation process signal and the edition process signal output from the output controller being displayed in real time on the displaying unit.

According to the configuration, on the same displaying unit, it is possible to display in real time not only biological information, but also information related to the edition process signal which is obtained by editing and processing the biological information. Therefore, it is possible not only to check the information related to the edition process signal while observing the condition of the subject, but also to take time-series correlation between all sets of other measured biological information and the information related to the edition process signal to compare them with each other, and to check relationships among them. Hence, a comprehensive comparative evaluation is enabled, and a diagnosis can be performed more rapidly and correctly. Moreover, a result of the comparison can be used as research data for a medical person.

The biological information measurement and display apparatus may further comprise: a library which is communicable with the first processor and the second processor, and which is configured to store custom application software, and the second processor may receive the calculation process signal through the library, and produce the edition process signal by using the custom application software.

According to the configuration, the edition process signal can be produced by using the custom application software. Therefore, desired data can be rapidly acquired, and the acquired data can be used in medical treatment for the subject or research by the medical person.

The edition process signal may be a signal which is produced by editing and processing a plurality of kinds of calculation process signals measured by a plurality of the measuring units.

According to the configuration, it is possible to display not only the calculation process signal related to existing biological information, but also the edition process signal related to a desired customize parameter which is obtained by editing and processing a plurality of calculation process signals. Therefore, each medical person can structure a new guideline by using a customize parameter which is based on the unique thinking of the person, and perform correct treatment. Moreover, the edition and processing in which the data amount related to a plurality of kinds of calculation process signals are performed on the second operating system. Irrespective of the operation state (stop due to freeze) of the second operating system, therefore, the calculation process signal related to biological information can be surely acquired by the first processor operating on the first operating system. Consequently, the security of the treatment on the subject can be ensured.

Display contents of the edition process signal may be displayed in a manner visually distinguishable from the display contents of the calculation process signal.

According to the configuration, the kind of the displayed information can be easily recognized, and the security of the procedure on the subject can be ensured.

Display contents of the edition process signal may be displayed in a circumferential region of the displaying unit.

According to the configuration, the display contents related to the calculation process signal which is continuously measured can be recognized easily and correctly, and the security of the procedure on the subject can be ensured.

According to the biological information measurement of the presently disclosed subject matter, the measurement function can be flexibly expanded while ensuring the reliability of the measurement operation.

What is claimed is:

1. A biological information measurement and display apparatus comprising:
   an apparatus body;
   a first operating system;
   a second operating system;
   a first processor which is configured to operate on the first operating system, and which is configured to arithmetically process biological information measured by a measuring unit, to produce a calculation process signal;
   a second processor which is configured to operate on the second operating system, which is communicable with the first processor, and which is configured to edit and process the calculation process signal transmitted from the first processor, to produce an edition process signal;
   an output controller which is configured to receive the calculation process signal produced by the first processor, and the edition process signal produced by the second processor, and which is configured to output the received calculation process signal and the received edition process signal; and
   a library which is communicable with the first processor and the second processor, and which is configured to store custom application software, wherein
   the calculation process signal and the edition process signal output from the output controller are displayed in real time on a displaying unit,
   the first operating system, the second operating system, the first processor, the second processor, and the output controller are housed in the apparatus body, and
   the second processor receives the calculation process signal through the library, and produces the edition process signal by using the custom application software.

2. The biological information measurement and display apparatus according to claim 1, wherein the edition process signal is a signal which is produced by editing and processing a plurality of kinds of calculation process signals measured by a plurality of the measuring units.

3. The biological information measurement and display apparatus according to claim 2, wherein display contents of the edition process signal are displayed in a manner visually distinguishable from the display contents of the calculation process signal.

4. The biological information measurement and display apparatus according to claim 2, wherein display contents of the edition process signal are displayed in a circumferential region of the displaying unit.

5. The biological information measurement and display apparatus according to claim 3, wherein display contents of the edition process signal are displayed in a circumferential region of the displaying unit.

6. The biological information measurement and display apparatus according to claim 1, wherein display contents of the edition process signal are displayed in a manner visually distinguishable from the display contents of the calculation process signal.

7. The biological information measurement and display apparatus according to claim 6, wherein display contents of the edition process signal are displayed in a circumferential region of the displaying unit.

8. The biological information measurement and display apparatus according to claim 1, wherein display contents of the edition process signal are displayed in a circumferential region of the displaying unit.

* * * * *